(12) United States Patent
Offer et al.

(10) Patent No.: US 7,527,978 B2
(45) Date of Patent: May 5, 2009

(54) FLOW CYTOMETRY BASED MICRONUCLEUS ASSAYS AND KITS

(75) Inventors: Tal Offer, Oakland, CA (US); Emily Ho, Corvalls, OR (US); Bruce N. Ames, Berkeley, CA (US); Frans Kuypers, Berkeley, CA (US)

(73) Assignee: Children's Hospital & Research Center at Oakland, Oakland, CA (US)

( * ) Notice: Subject to any disclaimer, the term of this patent is extended or adjusted under 35 U.S.C. 154(b) by 529 days.

(21) Appl. No.: 10/961,941

(22) Filed: Oct. 7, 2004

(65) Prior Publication Data

US 2006/0078949 A1 Apr. 13, 2006

(51) Int. Cl.
*G01N 33/533* (2006.01)
(52) U.S. Cl. .......................... 436/526; 435/6; 435/7.25; 435/7.94; 435/326; 435/355; 435/372; 435/287.2; 435/286.5; 436/508; 436/518; 436/521; 436/538; 436/10; 436/63; 436/177; 530/388.7
(58) Field of Classification Search ............ 435/6, 435/7.1, 7.2, 7.9, 7.92, 7.94, 334, 355, 968, 435/973, 7.25, 40.5, 326, 372, 286.5, 287.2; 436/501, 508, 512, 518, 521, 522, 526, 536, 436/94, 538, 10, 63, 177; 530/388.7
See application file for complete search history.

(56) References Cited

U.S. PATENT DOCUMENTS

| 5,447,842 | A | * | 9/1995 | Simons | 435/6 |
| 5,861,253 | A | * | 1/1999 | Asgari et al. | 435/6 |
| 5,906,915 | A | * | 5/1999 | Payrat et al. | 435/2 |
| 6,100,038 | A | * | 8/2000 | Dertinger et al. | 435/6 |
| 2003/0134305 | A1 | * | 7/2003 | Dertinger et al. | 435/6 |

OTHER PUBLICATIONS

Abramsson-Zetterberg et al. (Human Cytogenetic Biomonitoring Using Flow-Cytometric Analysis of Micronuclei in Transferrin-Positive Immature Peripheral Blood Reticulocytes, Environmental and Molecular Mutagenesis 36: 22-31 (2000)).*

Lemmer E R. et al., Isolation from human fetal liver of cells co-expressing CD34 haematopoietic stem cell and CAM 5.2 pancytokeratin markers, Journal of hepatology, (Sep. 1998) vol. 29, No. 3, pp. 450-454).*

* cited by examiner

*Primary Examiner*—Gailene R Gabel
(74) *Attorney, Agent, or Firm*—Richard Aron Osman

(57) ABSTRACT

The invention is a method for analyzing immature reticulocytes for the presence of micronuclei. The method includes reticulocyte enrichment, fluorescent labeling, micronuclei staining, and analysis using single-laser flow cytometry. The invention also includes kits containing reagents to use in the method.

14 Claims, No Drawings

FLOW CYTOMETRY BASED MICRONUCLEUS ASSAYS AND KITS

FIELD OF THE INVENTION

The field of the invention is a single-laser flow-cytometry based assays and kits to measure micronuclei in immature reticulocytes.

BACKGROUND OF THE INVENTION

Exposure to environmental stress such as radiation, poor nutrition or smoking, can cause chromosome breaks, the most hazardous lesion formed by radiation. The micronucleus test is an established method to analyze in vivo chromosomal damage and has been used by many investigators to monitor DNA integrity following exposure to poor nutrition, toxicants and other stressors. The test is based on the observation that a secondary nucleus (micronucleus) is formed around a chromosomal fragment, outside the main nucleus of a dividing cell. A micronucleus may also be produced due to a lagging whole chromosome formed as a result of a chromosome loss at anaphase. The measurement of micronuclei (MN) in peripheral blood lymphocytes has been a conventional tool to biomonitor human populations for DNA damage, and is widely used in product development to fulfill regulatory requirements for assessment of chromosomal damage (Fenech, M., Mutat Res (2000) 455:81-95; Fenech, M., Drug Discov Today (2002) 7:1128-1137). The lymphocyte assay applies a chemical to block cytokinesis after a single cell division and the MN are manually counted and scored using microscopy (Xue et al, Int J Cancer (1992) 50:702-705; Fenech et al, Environ Mol Mutagen (1997) 30:112-118). Although this is a low throughput assay it allows detection of other DNA-damage markers, such as nucleoplasmic bridges and nuclear buds and is effective in scoring 1000 cells for effects of folate deficiency and ionizing radiation. The mitogenic response is also indicative of immune responsiveness. However, to reliably detect small increases in MN frequency in people at risk, monitoring of a large number of cells in exposed and control groups is required. To accomplish this, a simple assay that enables scoring of large number of cells in short periods of time should be performed.

A powerful assay in detecting small changes in genome damage in animal models is the mouse in vivo erythrocyte MN test (Mavournin et al., Mutat Res (1990) 239:29-80). Micronuclei are particularly apparent in red blood cells (RBC), which otherwise lack DNA. During erythropoiesis, a hematopoietic stem cell differentiates into an erythroblast, and then expels its nucleus to become a reticulocyte. The newly formed reticulocyte is then released from the bone marrow into the bloodstream, where it develops into a mature erythrocyte. Although the main nucleus is lost during reticulocyte formation, micronuclei are retained in the reticulocyte cytoplasm (Fenech, M., 2000). Dertinger et al have developed an in vivo rodent micronucleus test for detecting micronucleated reticulocytes by flow cytometry using fluorescent labels for transferrin receptor (CD71) and fluorescent DNA stains such as propidium iodide (Mutat Res (1996) 371:283-292).

In humans, in contrast to mice, micronucleated erythrocytes are soon filtered from the circulating blood by the spleen and therefore are not generally available for analysis. Abramsson-Zetterberg et al have described a method to measure MN in an enriched peripheral-blood reticulocyte-population (Environ Mol Mutagen (2000) 36:22-31). With this method, Hoechst 33342 and thiazole orange were used to stain DNA and RNA, respectively. They showed that MN frequency in reticulocytes approximate those observed in bone marrow. However their method includes multiple laborious steps and required the use of a dual-laser flow cytometer with a UV laser to excite the Hoechst 33342 fluorochrome. This type of flow cytometer is more specialized and not widely available in common laboratory settings. Similar to the in vivo rodent micronucleus test, Dertinger et al. further improved the scoring of micronucleated reticulocytes in humans to enable the use of widely available bench top instruments (Mutat Res (2002) 515:3-14; Mutat Res (2003) 542: 77-87). However, their procedure required long data-collection times.

We have developed a simple method to isolate and analyze immature reticulocytes in the peripheral blood for the presence of micronuclei that is useful in establishing the relation between environmental stress (e.g. micronutrient deficiencies) and chromosomal damage. This method enables rapid analysis of large numbers of cells by applying single-laser flow-cytometry to measure micronuclei in an enriched transferrin-positive reticulocyte population.

RELEVANT LITERATURE

Dertinger et al, Mutat Res (2002) 515:3-14
Dertinger et al, Mutat Res (2003) 542:77-87.
Dertinger et al, U.S. Pat. No. 6,100,038
Abramsson-Zetterberg et al, Environ Mol Mutagen (2000) 36:22-31

SUMMARY OF THE INVENTION

One aspect of the invention is a method for analyzing immature reticulocytes for the presence of micronuclei. The method comprising the steps of: a) immuno-magnetically isolating reticulocytes from a human blood cell sample by contacting the sample with first reticulocyte surface protein—selective first antibody coated, flow cytometry-compatible magnetic beads under conditions that allow the first antibody to selectively bind the reticulocytes, applying a magnetic field to the sample to magnetically segregate antibody-bound reticulocytes, and washing away unsegregated material; b) labeling the reticulocytes with a fluorescently labeled second reticulocyte surface protein—selective second antibody; c) staining reticulocyte micronuclei with a DNA—staining fluorescent dye, wherein the dye and the second antibody have overlapping absorption spectra, and distinguishable emission spectra; and d) analyzing the labeled reticulocytes for the presence of stained micronuclei using single-laser flow cytometry.

In one embodiment of the invention, the first and second reticulocyte surface proteins are independently selected from the group consisting of transferrin receptor (CD71), glycophorin A (CD235a), thrombospondin (TSP) receptor (glycoprotein IV; CD36), and integrin $\alpha 4\beta 1$ (very late activation antigen-4 (VLA-4), and CD49d/CD29). In further embodiments, the first reticulocyte surface protein is selected from the group consisting of CD71, CD36, and CD49d/CD29; and the second reticulocyte surface protein is selected from the group consisting of CD71, CD235a, CD36, and CD49d/CD29.

In further embodiment of the invention, the beads are polynucleotide-free and have a diameter of 1 μm. In a further embodiment, the beads are BIOMAGAnti-CD71 beads (BIOMAG is a trademark of Polysciences, Warrington, Pa.).

In one embodiment of the invention, the sample is whole peripheral blood. In an alternate embodiment, the sample is obtained by centrifuging whole blood and discarding plasma and buffy coat layers from the sample.

In additional embodiments of the invention, the second antibody is labeled with fluorescein isothiocyanate (FITC), the DNA staining dye is 7-aminoactinomycin D, and the labeled and stained reticulocytes are analyzed using argon ion laser.

Another aspect of the invention is a kit for analyzing immature reticulocytes for the presence of micronuclei. The kit comprises premeasured, separately packaged and labeled amounts of a first reticulocyte surface protein—selective first antibody coated flow cytometry-compatible magnetic beads; and premeasured, separately packaged and labeled amounts of a fluorescently labeled second reticulocyte surface protein—selective second antibody. In one embodiment, the first and second surface proteins are independently selected from the group consisting of transferrin receptor (CD71), glycophorin A (CD235a), thrombospondin (TSP) receptor (glycoprotein IV; CD36), and integrin $\alpha 4\beta 1$ (very late activation antigen-4 (VLA-4), and CD49d/CD29). In more specific embodiments, the first reticulocyte surface protein is selected from the group consisting of CD36, CD71, and VLA4, and the second reticulocyte surface protein is CD71.

In one specific embodiment, the beads provided with the kit have a diameter of 1 μm. The kit may additionally comprise premeasured, separately packaged and labeled amounts of a DNA—staining fluorescent dye; wherein the dye and the second antibody have overlapping absorption spectra, and distinguishable emission spectra. In one embodiment, the second antibody is labeled with fluorescein isothiocyanate (FITC), and the dye is 7-aminoactinomycin.

DETAILED DESCRIPTION OF EMBODIMENTS OF THE INVENTION

Exposure to environmental stress such as radiation, poor nutrition or smoking, can cause hazardous lesions in DNA including double-strand breaks (DSB). In red blood cells, a DNA fragment or lagging chromosome forms a micronucleus when left behind after the main nucleus is extruded to form the mature reticulocyte during erythropoiesis. Reticulocytes with micronuclei in human peripheral blood are not generally available for analysis because the spleen removes aberrant cells. We have developed a simple and rapid method to isolate and analyze immature reticulocytes in the peripheral blood for the presence of micronuclei before these cells are removed by the spleen. This method applies single-laser flow-cytometry to measure micronuclei in an enriched reticulocyte population. Heavy smoking is associated with increased micronuclei frequency, due to DSBs. We assessed DNA damage in smokers using this novel flow-cytometry based micronuclei-assay. Our results show that this assay can effectively detect micronuclei in human blood samples. This method, unlike available micronuclei assays, allows rapid evaluation of a large number of cells, and provides an improved technology for monitoring human populations for genetic damage.

Our invention provides methods and kits for analyzing immature reticulocytes for the presence of micronuclei. In one embodiment, the method generally comprises the steps of immuno-magnetically isolating reticulocytes from a human blood cell sample by contacting the sample with flow cytometry-compatible magnetic beads coated with a reticulocyte surface protein—selective antibody, under conditions wherein the antibody selectively binds the reticulocytes; applying a magnetic field to the sample to magnetically segregate antibody-bound reticulocytes; washing away unsegregated material; labeling the reticulocytes with a fluorescently labeled reticulocyte surface protein—selective antibody; staining reticulocyte micronuclei with a DNA—staining fluorescent dye, wherein the dye and the fluorescently labeled antibody have overlapping absorption spectra, and distinguishable emission spectra; and analyzing the labeled reticulocytes for the presence of stained micronuclei using single-laser flow cytometry.

One advantage of our method over prior methods is that the magnetic beads are flow cytometry-compatible, and do not have to be removed from segregated cells prior to flow cytometry analysis. Thus, no time-consuming bead detachment and separation procedures are required. Flow cytometry-compatible beads are sufficiently small as to not clog the flow cytometry equipment and, during analysis are either distinguishable from the cells or do not influence the scatter properties of the isolated cell population. Generally suitable beads have a diameter in a range of about 0.05-4.0 μm, preferably in a range of about 0.08 to 2.0 μm, more preferably, a diameter of about 1.0 μm.

The beads are coated with a reticulocyte surface protein—selective antibody. A suitable reticulocyte surface protein is one that is expressed by reticulocytes, and not expressed by at least one other blood cell type present in the sample, such that the immuno-magnetic isolation step results in a magnetically segregated cell population that is reticulocyte-enriched relative to the starting cell sample. Examples of targetable reticulocyte surface proteins include the transferrin receptor (CD71), glycophorin A (CD235a), thrombospondin (TSP) receptor (glycoprotein IV; CD36), and integrin $\alpha 4\beta 1$ (very late activation antigen-4 (VLA-4); CD49d/CD29). Preferably, the surface protein is not expressed on mature erythrocytes (e.g. VLA-4 and CD71) or is expressed on mature erythrocytes at very low levels (e.g. CD36). These and other reticulocyte surface proteins that have reduced expression on mature erythrocytes have been described in the literature (see Geminard et al, Biocell (2002) 26:205-215; Rabesandratana et al, Blood (1998) 91:2573-2580; and Covas et al, Haematologica (2004) 89:273-280). In a particularly preferred embodiment, the surface protein is CD71.

Uncoated magnetic beads can be purchased and coated with the desired antibody prior to use using well-known protocols. Alternatively, commercially available flow cytometry-compatible beads precoated with a suitable antibody can be used. Examples of commercially available, precoated beads include CD71 Microbeads (Miltenyi Biotec Inc., Auburn, Calif.), CD235a (Glycophorin A) MicroBeads (Miltenyi Biotec Inc.), and Dynabeads® CD71 (Dynal Biotech LLC, Brown Deer, Wis.). Presently preferred beads are the BioMag® SelectaPure™ Anti-CD71 Antibody beads (Polysciences, Warrington, Pa.), which have a diameter of about 1.0 μm. With some commercially available beads, the antibodies are attached to the bead via a polynucleotide linker, which after cell capture, can be treated with a suitable enzyme to release the cells from the bead. However, because the method of the invention uses flow cytometry-compatible beads, there is no need for bead removal. Further, a polynucleotide linker may become labeled in the staining step of the method, resulting in interference. Thus, the beads used are preferably polynucleotide-free.

Any human blood cell sample can be used in the methods of the invention, such as whole peripheral blood, and samples obtained from bone marrow and peripheral blood. Because of ease of collection, samples obtained from peripheral blood are preferred. Alternatively, prior to the immuno-magnetic isolation step, red blood cells can be separated by centrifuging whole blood and discarding the plasma and buffy coat layers. The blood cell sample is then contacted with the antibody coated, flow cytometry-compatible magnetic beads under conditions that allow the antibody to bind the reticulocytes. A magnetic field is then applied to magnetically segregate antibody-bound reticulocytes, and unsegregated material is washed away. Preferred conditions for binding cells to the antibody/beads, magnetic segregation, and washing away of unsegregated material, may be detailed in commercial magnetic bead product data sheets, are generally known in the art, and may be further optimized using routine experimentation.

The reticulocytes are labeled with a fluorescently labeled antibody that is selective for a reticulocyte surface protein, particularly the surface proteins discussed above. The reticulocytes can be labeled at any time prior to flow cytometry analysis; however, labeling is preferably done after the reticulocytes have been isolated from the sample, which reduces the amount of labeling reagent used. The fluorescently labeled antibody (referred herein as "second antibody") may be selective for the same surface protein as the antibody (referred herein as "first antibody") coated on the beads. Alternatively, the first and second antibodies may be directed against different first and second surface proteins, respectively. If the first antibody does not distinguish reticulocytes from mature erythrocytes (e.g. anti-CD235a), then the second antibody used preferably does not bind mature erythrocytes (e.g. anti-CD71). In one preferred embodiment, the first reticulocyte surface protein is CD71, CD36, or CD49d/CD29; and the second reticulocyte surface protein is CD71, CD235a, CD36, or CD49d/CD29. In a further preferred embodiment, both the first and second reticulocyte surface proteins are CD71.

The second antibody is labeled with a fluorescent molecule suitable for use in flow cytometry. Numerous suitable fluorescent molecules are commercially available from various reagent companies (e.g. Molecular Probes, Eugene, Oreg.), including allophycocyanin (APC), 7-amino-4-methyl-coumarin-3-acetic acid (AMCA), BODIPY® FL, Cascade Blue, fluorescein isothiocyanate (FITC), phycoerythrin B (PE-B), phycoerythrin R (PE-R), rhodamine B-isothiocyanate (RITC), Texas Red, and tetramethylrhodamine isothyocyanate (TRITC). Procedures for conjugation of antibodies to fluorescent molecules are routine, and are often detailed in the product data sheets for the fluorescent molecules. Conveniently, fluorescently labeled antibodies selective for reticulocyte surface proteins are available commercially. Examples include anti-human glycophorin A-PE, anti-human glycophorin A FITC, and anti-human CD71 FITC (each from Stemcell Technologies, Vancouver, BC Canada); and monoclonal anti-human CD49d (VLA-4)/R-PE, monoclonal anti-human CD29 (b1 integrin)/R-PE, and monoclonal anti-human CD36/FITC (each from Ancell, Bayport, Minn.). In a preferred embodiment, the second antibody is fluorescently labeled with FITC. In a further preferred embodiment, the second antibody is labeled with FITC and is selective for CD71.

Prior to flow cytometry analysis, reticulocyte micronuclei are stained with a DNA—staining fluorescent dye having overlapping absorption spectra with the fluorescently labeled second antibody, but distinguishable emission spectra. Numerous suitable DNA—staining fluorescent dyes are commercially available from various reagent companies (e.g. Molecular Probes, Eugene, Oreg.), including 7-aminoactinomycin D (7-AAD), acridine orange, bisbenzimide, BOBO-1, BOBO-3, chromomycin A3, DAPI, ethidium bromide, Hoechst 33258, Hoechst 33342, Hoescht 33245, LDS 751, mithramycin, propidium iodide (PI), pyronine, SYTOX Blue, SYTOX Green, SYTOX Orange, TO-PRO-1, TOTO-1, TOTO-3, YOYO-1, and YOYO-3. Information on the absorption and emission spectra of DNA—staining dyes is readily available and known to those skilled in the art. In one preferred embodiment, the second antibody is labeled with FITC, which has peak excitation and emission wavelengths of approximately 490 nm and 520 nm, respectively, and the DNA—staining dye is 7-AAD, which has peak excitation and emission wavelengths of approximately 555 nm and 655 nm, respectively. In another preferred embodiment, the second antibody is labeled with PE, and/or the DNA—staining dye is PI.

Certain dyes, such as DAPI and bisbenzimide, selectively bind double stranded DNA, and thus result in little background staining of the cytoplasm. Other dyes such as 7-AAD, PI, and pyronine bind to RNA as well as DNA. Thus, the reticulocytes are treated with RNase to degrade RNA and prevent its staining from interfering with analysis of the micronuclei. The RNA degrading step can be done any time prior to flow cytometry analysis; however, RNase treatment is preferably done after the reticulocytes have been isolated from the sample to reduce the amount of labeling RNase required.

Certain DNA staining dyes, such as 7-AAD, chromomycin A3, and SYTOX Green are relatively cell-impermeable, and thus prior to staining, the cell sample must be permeabilized, for example, by suspending the cells in cold methanol.

To date, most micronuclei assays do not distinguish between aneugenic and clastogenic effects resulting in lagging chromosomes or fragments, respectively. Because various genotoxic exposures may induce only one type of micronuclei, a specific analysis of the type of micronuclei further improves the sensitivity of detecting exposure effects. Thus, in one embodiment, the method additionally comprises, prior to flow cytometry analysis, the step of labeling micronuclei centromeres or kinetochores with a fluorescent probe having overlapping absorption spectra with the fluorescently labeled second antibody, but distinguishable emission spectra. In one preferred embodiment, the probe is a fluorescently labeled peptide nucleic acid (PNA) that binds to centromere protein B (CENP-B).

After the reticulocytes to be analyzed have been isolated, labeled, and stained, they are analyzed for the presence of stained micronuclei using single-laser flow cytometry. Samples are analyzed on a suitable single laser flow cytometer equipped with standard optics. In a preferred embodiment, the labeled reticulocytes are analyzed using an argon ion laser (e.g. FACSort™, Becton Dickinson, Sunnyvale, Calif.). A live gate is used in the forward/side scatter parameters to exclude debris and residual nucleated cells, thereby restricting data acquisition mostly to immature reticulocytes. Any applicable commercially available software for flow cytometry data acquisition and analysis (e.g. CellQuest, Largo, Fla.) can be used for analysis. In a typical analysis, quadrant plot-regions of interest are defined for red blood cells, non-micronucleated reticulocytes, and micronucleated reticulocytes, and the number of events in each region is determined and the relative frequencies are calculated.

The invention further provides kits for analyzing immature reticulocytes for the presence of micronuclei. The kit generally comprises combinations of two or more of the reagents discussed above that can be used together in practicing the method of the invention. The reagents are premeasured, separately packaged and labeled, and are preferably accompanied with instructional material on how the reagents are used to: i) immuno-magnetically isolate reticulocytes from a human blood cell sample, ii) fluorescently label the reticulocytes, iii)

stain reticulocyte micronuclei, and iv) analyze the labeled reticulocytes for the presence of stained micronuclei using single-laser flow cytometry.

In one embodiment, the kit comprises premeasured, separately packaged and labeled amounts of a first reticulocyte surface protein—selective first antibody coated flow cytometry-compatible magnetic beads and premeasured, separately packaged and labeled amounts of a fluorescently labeled second reticulocyte surface protein—selective second antibody. In a specific embodiment, the first and second surface proteins are independently selected from the group consisting of transferrin receptor (CD71), glycophorin A (CD235a), thrombospondin (TSP) receptor (glycoprotein IV; CD36), and integrin $\alpha 4\beta 1$ (very late activation antigen-4 (VLA-4), and CD49d/CD29).

The kit may optionally include premeasured, separately packaged and labeled amounts of a DNA—staining fluorescent dye. When the DNA—staining dye is provided, it and the second antibody will have overlapping absorption spectra, and distinguishable emission spectra, as described above with respect to the method of the invention. In one preferred embodiment, the dye is 7-AAD. In one preferred embodiment, the magnetic beads of the kit have a diameter of 1 µm. In other preferred embodiments, the first reticulocyte surface protein is CD36, CD71, or VLA-4, and the second reticulocyte surface protein is CD71. In a further preferred embodiment, the second antibody is labeled with fluorescein isothiocyanate (FITC). In a further preferred, specific embodiment, the kit includes premeasured, separately packaged and labeled amounts of 7-AAD, the first and second surface proteins are both CD71, the magnetic beads have a diameter of 1 µm, and the second antibody is labeled with fluorescein isothiocyanate (FITC).

EXAMPLES

Study Population. The Institutional Review Boards at Children's Hospital and Research Center at Oakland and Oregon State University approved this study. All participants provided informed consent prior to enrollment in the study. Blood samples were collected in 10 ml EDTA vacutainer tubes by venipuncture by a certified phlebotomist.

Thirty-two volunteers (15 females, 17 males) participated in the study. Smokers (7 females, 10 males) were selected based on number of cigarettes smoked on daily basis. Occasional smokers (smokers who did not smoke every day) were excluded from the study. Nonsmokers (8 females, 7 males) were selected based upon never smoking and currently not residing with a smoker. The participants had no history of taking any dietary supplements within the last year. Routine serum blood chemistry assays were performed at Good Samaritan Hospital (Corvallis, Oreg.). All serum chemistries were within normal limits for all studied participant.

Reticulocyte Enrichment. Immuno-magnetic separation was used to isolate and enrich CD71 young reticulocytes from whole blood samples. To separate the RBCs from whole blood prior to enrichment, samples were centrifuged at 1400 rpm for 5 minutes and the plasma and buffy coat were removed. Approximately 1 ml of RBCs was incubated with BioMag™ Anti-CD71 beads (Polysciences, Inc, Warrington, Pa.) at 0.5 mg/ml for 30 minutes at room temperature. Samples were mixed every 10 minutes during this incubation period. This procedure selectively isolates immature reticulocytes that express the transferrin receptor (CD71).

To separate reticulocytes from mature RBCs, samples were placed in an MPC-S magnet (Dynal Biotech Inc., WI USA) for 15 minutes and washed three times with HEPES-buffered saline solution (HBS) (purchased from USB, Cleveland, Ohio)/5% FBS. Following final wash, cells were resuspended in HBS/5% FBS in a final volume of 200 µl. The enriched reticulocytes were labeled with 10% CD71-FITC antibody (BD-Pharmingen, Santa Clara, Calif.) and resuspended in 100 µl heparinized HBS (500 units/ml heparin; Sigma, St. Louis, Mo.). Samples were then fixed by forcefully pipetting solution into 1 ml of ultra-cold (−80° C.) methanol (Fisher Scientific, Springfield, N.J.). Samples were stored at −80° C. until analysis.

Micronuclei Staining. The fixed/permeabilized cells were rehydrated in 10 ml of HBS and subsequently, RNase (Sigma, St. Louis, Mo.) at 3 mg/ml was added to remove RNA from the cell and prevent RNA-nucleotide staining. Then, 10 µg/ml 7-aminoactinomycin D (7-AAD; Molecular Probes, Eugene, Oreg.) was added and incubated with the cells for 30 minutes in dark to label DNA before flow cytometric analysis. The DNA dye used stains nucleotides nonspecifically and thus also labels leukocyte DNA. To prevent overlap of leukocyte events with micronuclei in the analysis file the leukocyte population, which appears in a separate area in the forward/side scatter, were gated out during analysis. The leukocyte population was located in a preliminary experiment using CD45-FITC antibody (BD-Pharmingen, Santa Clara, Calif.). The position of the quadrant used to distinguish between transferrin-positive reticulocytes (trf-ret) and mature erythrocytes (RBCs) was set by running a control sample unlabeled for CD71.

Flow Cytometry. Samples were analyzed on an argon ion laser FACSort (Becton Dickinson, Sunnyvale, Calif.) equipped with standard optics. A live gate was used in the forward/side scatter parameters to exclude debris and residual nucleated cells, thereby restricting data acquisition mostly to trf-ret population. Quadrants were defined based on control samples of unlabeled trf-ret and FITC labeled trf-ret (not stained with a DNA dye). During acquisition, data from about 200,000 trf-ret was acquired. CellQuest software was used for data acquisition and analysis. In the analysis, quadrant plot-regions of interest were defined for RBCs, trf-ret and micronucleated trf-ret (MN-trf-ret). The number of events in each region was determined and the relative frequencies were calculated from the number of events in the upper right quadrant divided by the total number of events in the upper-quadrant plot regions that includes the trf-ret.

Effect of Smoking. Unpaired two-tailed t-test was performed to assess the differences in MN frequencies between nonsmokers and smokers. Differences in means between the two groups were tested using Tukey's test. Level of significance was evaluated at $p<0.05$. There was a significant increase in MN-trf-ret in smokers (n=17) compared to nonsmokers (n=15). To examine interassay differences, donors were sampled 3 times over a period of 4 months. The MN frequencies were quite stable over this period, with values of (mean±SD) 0.096+0.026 for a heavy smoker (25 cigarettes/day) and 0.014+0.004 for a typical nonsmoker.

Our data show that our assay can effectively detect a small increase in MN frequency in peripheral blood of people exposed to smoking. The practical importance of this assay is emphasized by the projected statistical power for detection of an increase in 1 micronucleus per 1000 cells. For type I error=5%, assuming standard deviation of 0.3 MN/1000 cells within a group (the observed standard deviation of smokers) 4 subjects per group would yield a statistical power of 99% to detect an increase of 1 MN/1000 cells. If assuming a standard deviation to be as great as 0.5 MN/1000 cells within a group, 4 subjects per group would yield a statistical power of 80% to detect a difference of 1 MN/1000 cells between groups while 10 subjects would be sufficient to yield a statistical power of 99%.

With the present method an experienced person using 4 MPC-S units for separation can operate 24 samples in less than 4 hours, or at least 48 samples per day. Staining of the fixed samples including the RNase treatment takes approximately 1 hour. The time required to collect data on a single-laser flow cytometer is between 1-2 minutes per sample, or over 100 samples a day. Combining of the enrichment approach with the high throughput nature of the scoring system allows for more trf-ret to be assessed for MN and improves the sensitivity of the method.

The assay is simple and enables short data acquisition times with the requirement of single-laser flow cytometer, which is readily available in most laboratory settings. Therefore, this assay provides an excellent tool for genetic monitoring of human populations. Since many vitamin and mineral deficiencies lead to chromosome breaks, this assay is of particular utility in studies examining nutrition and cancer prevention.

The foregoing examples and detailed description are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for analyzing immature reticulocytes for the presence of micronuclei comprising the steps of:
    a) immuno-magnetically isolating reticulocytes from a human blood cell sample by contacting the sample with first reticulocyte surface protein—selective first antibody coated, flow cytometry-compatible magnetic beads, under conditions wherein the first antibody selectively binds the reticulocytes, applying a magnetic field to the sample to magnetically segregate antibody-bound reticulocytes, and washing away unsegregated material;
    b) labeling magnetic bead-bound reticulocytes of step a) with a fluorescently labeled second reticulocyte surface protein—selective second antibody;
    c) permeabilizing the magnetic bead-bound reticulocytes of step b) to an RNase and a DNA-staining fluorescent dye, and then treating the reticulocytes with the RNase to prevent RNA-staining from interfering with analysis of the micronuclei and staining micronuclei of the reticulocytes with the DNA-staining fluorescent dye, wherein the dye and the fluorescently-labeled second antibody have overlapping absorption spectra, and distinguishable emission spectra; and
    d) analyzing the labeled magnetic bead-bound reticulocytes of step c) for the presence of stained micronuclei using single-laser flow cytometry;
    wherein the first and second reticulocyte surface proteins are independently selected from the group consisting of transferrin receptor (CD71), glycophorin A (CD235a), thrombospondin (TSP) receptor (glycoprotein IV; CD36), and integrin α4β1(very late activation antigen-4(VLA-4), and CD49d/CD29).

2. The method of claim 1 wherein the beads have a diameter of 1 μm.

3. The method of claim 1 wherein the first reticulocyte surface protein is selected from the group consisting of CD36, CD71, and VLA-4.

4. The method of claim 1 wherein the first reticulocyte surface protein is CD71.

5. The method of claim 1 wherein the beads are BIOMAG Anti-CD71 beads (BIOMAG is a trademark of Polysciences, Warrington, Pa.).

6. The method of claim 1 wherein the beads are polynucleotide-free.

7. The method of claim 1 wherein the sample is whole peripheral blood.

8. The method of claim 1 wherein the sample is obtained by centrifuging whole blood and discarding plasma and buffy coat layers from the sample.

9. The method of claim 1 wherein the first reticulocyte surface protein is selected from the group consisting of CD71, CD36, and CD49d/CD29; and the second reticulocyte surface protein is selected from the group consisting of CD71, CD235a, CD36, and CD49d/CD29.

10. The method of claim 1 wherein the second reticulocyte surface protein is CD71.

11. The method of claim 1 wherein the second antibody is labeled with fluorescein isothiocyanate (FITC).

12. The method of claim 1 wherein the DNA staining dye is 7-aminoactinomycin D.

13. The method of claim 1 wherein in the analyzing step, an argon ion laser is used.

14. The method of claim 1 wherein: the sample is obtained by centrifuging whole blood and discarding plasma and buffy coat layers from the sample, the first and second surface proteins are both CD71, the beads are polynucleotide-free and have a diameter of 1 μm, the second antibody is labeled with FITC, the DNA staining dye is 7-aminoactinomycin D, and an argon ion laser is used in the analyzing step.

* * * * *